Figure 3A:
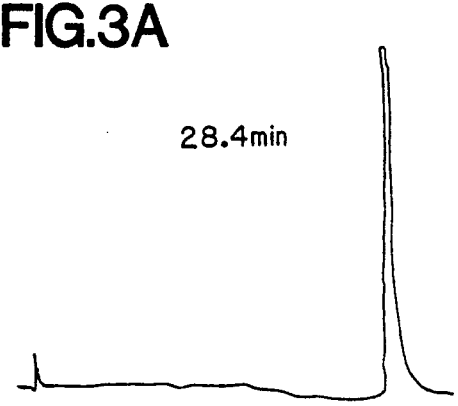

United States Patent [19]

Groody

[11] Patent Number: 5,071,974
[45] Date of Patent: Dec. 10, 1991

[54] COMPOSITIONS AND METHODS FOR THE SYNTHESIS OF OLIGONUCLEOTIDES HAVING 5'-PHOSPHORYLATED TERMINI

[75] Inventor: E. Patrick Groody, Naperville, Ill.

[73] Assignee: Amoco Corporation, Chicago, Ill.

[21] Appl. No.: 926,010

[22] Filed: Oct. 31, 1986

[51] Int. Cl.$^5$ .............................................. C07H 19/00
[52] U.S. Cl. ........................................ 536/27; 536/28; 536/29
[58] Field of Search .................. 536/27, 28, 29; 435/6

[56] References Cited

U.S. PATENT DOCUMENTS

| | | | |
|---|---|---|---|
| 3,524,846 | 8/1970 | Moffatt et al. | 536/28 |
| 4,415,732 | 11/1983 | Caruthers et al. | 536/27 |
| 4,500,707 | 2/1985 | Caruthers et al. | 536/28 |
| 4,757,141 | 6/1988 | Fung et al. | 536/27 |
| 4,762,779 | 8/1989 | Snitman | 435/6 |

FOREIGN PATENT DOCUMENTS

| | | | |
|---|---|---|---|
| 8500816 | 2/1985 | Fed. Rep. of Germany | 536/27 |
| 3507881 | 9/1986 | Fed. Rep. of Germany | 536/28 |

OTHER PUBLICATIONS

Smith et al., Nucleic Acids Research, 13, 2399-2412 (1985).
McBride et al., Tetrahedron Letters, 24, 245-248 (1983).
Beaucage et al., Tetrahedron Letters, 22, 1859-1862 (1981).

Primary Examiner—Johnnie R. Brown
Assistant Examiner—L. Eric Crane
Attorney, Agent, or Firm—Norval B. Galloway; William H. Magidson; Ralph C. Medhurst

[57] ABSTRACT

Methods for the chemical 5' phosphorylation of oligonucleotides. An embodiment of the present invention includes reacting the 5' terminus of an oligonucleotide with a composition represented by the formula:

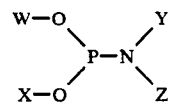

wherein if Y and Z are taken separately, each represent an alkyl, aryl, arylalkyl, cycloalkyl or cycloalkylaryl; or if Y and Z are taken together, Y and Z form an alkyl or alkylene chain with both terminal valence bonds of said chain being attached to the nitrogen atom to which Y and Z are attached; or if Y and Z are taken together, with the nitrogen atom, Y and Z form a nitrogen heterocycle including at least one additional heteroatom selected from the group consisting of nitrogen, oxygen, and sulfur. W and X are selected from the group of functional groups subject to nucleophilic attack or β-elimination and are removed.

15 Claims, 3 Drawing Sheets

FIG. 1A — 28.4 min
FIG. 1B — 29.4 min
FIG. 1C — 28.2 min

FIG.2A 24.3 min
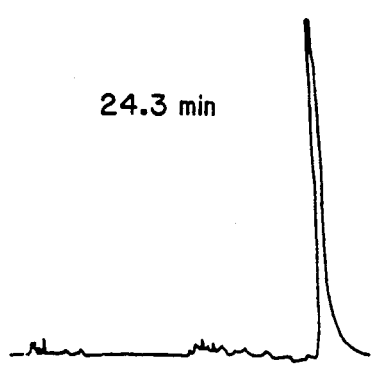
FIG.2D 27.7 min
FIG.2B 26.0 min
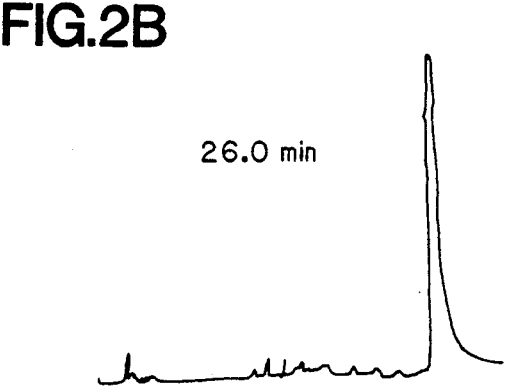
FIG.2E 28.4 min
FIG.2C 26.0, 28.3 min
FIG.2F 27.9 min
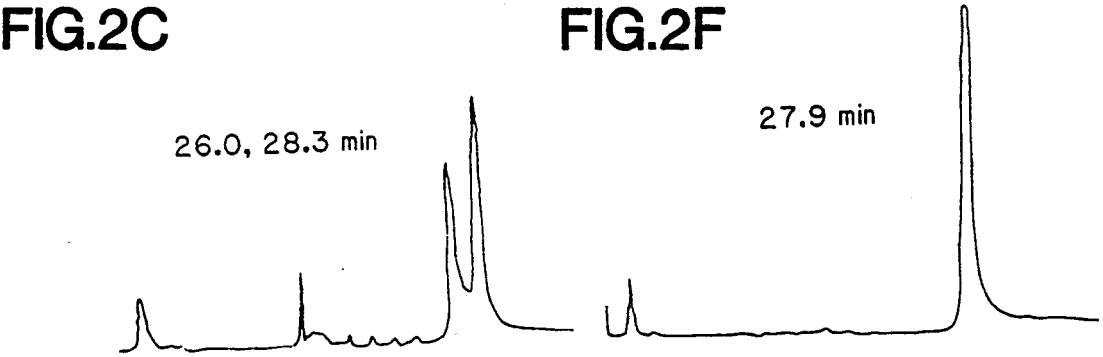

28.4 min 29.4 min 29.4 min 29.5 min 29.2 min

COMPOSITIONS AND METHODS FOR THE SYNTHESIS OF OLIGONUCLEOTIDES HAVING 5'-PHOSPHORYLATED TERMINI

The present invention pertains to compositions and methods for the use and synthesis of the compositions. More particularly, the present invention includes compositions and methods for phosphorylating the 5'termini of oligonucleotides.

Genetic information is stored in living cells in thread like molecules of deoxyribonucleic acid (DNA). In vivo, the DNA molecule is a double helix, each strand of which is a chain of nucleotides. Each nucleotide is characterized by one of four bases: adenine (A), guanine (G), thymine (T), cytosine (C). The bases are complimentary in the sense that due to the orientation of functional groups, certain base pairs attract and bond to each other through hydrogen bonding. Adenine in one strand of DNA pairs with thymine in an opposing complimentary strand. Guanine in one strand of DNA pairs with cytosine in an opposing complimentary strand. In ribonucleic acid (RNA), the thymine base is replaced by uracil (U) which pairs with adenine in an opposing complimentary strand.

DNA consists of covalently linked chains of deoxyribonucleotides and RNA consists of covalently linked chains of ribonucleotides. The genetic code of a living organism is carried upon the DNA strand in the sequence of the base pairs.

Each nucleic acid is linked by a phosphodiester bridge between the 5' hydroxyl group of the sugar of one nucleotide and the 3' hydroxyl group of the sugar of the adjacent nucleotide. Thus, each linear strand of DNA or RNA has one terminal end at a 5' hydroxyl group position and another terminal end at a 3' hydroxyl group position. The terminal ends of polynucleotides are often referred to as being 5' termini or 3' termini in reference to respective free hydroxyl group position. Naturally occurring DNA and RNA include a phosphate group at the 5' terminal hydroxyl position.

The development of phosphoramidite chemistry has facilitated the routine synthesis of oligonucleotides of a defined sequence. However, most synthetic DNA fragments are isolated with a free 5' hydroxyl group. For many biological applications, it is advantageous to directly isolate DNA having a 5' phosphate group.

A variety of enzymatic and chemical methods have been developed for the introduction of a 5' phosphate group. Examples of enzymatic or chemical modification of synthetic DNA to introduce a 5' phosphate group are disclosed in Nadeau, J. G., Singleton, C. K., Kelly, G. B., Weith, H. L., and Gough, G. R. (1984) Biochem. 23, 6153-6159; van der Marel, G. A., van Boeckel, C. A. A., Wille, G., and van Boom, J.H. (1982) Nucl. Acids Res. 10, 2337-2351; Gough, G. R., Bruden, M. J., Nadeau, J. G., amd Gilham, P. T. (1982) Tetrahedron Lett. 23, 3439-3443; van Boom, J. H., Grea, R., Luyten, W. C. and Vink, A. B., (1985) Tetrahedron Lett., 2779-2782; Yoshikawa, M., Skuraba, M., and Kusashio, K. (1970) Bull. Chem. Soc Jap., 456-461; and, Yoshikawa, M., Tetsuya, K., and Tadao, T. (1969) Bull. Chem. Soc. Jap., 3505-3508.

Although enzymatic methods are widely used, they are impractical for large scale work. The presently available chemical methods also have disadvantages which make them impractical for routine use. Most of these methods are incompatible with automated synthesizers due to the instability and corrosive nature of the required reagents. In addition, low yields are frequently encountered during the phosphorylation and deblocking steps.

DESCRIPTION OF THE INVENTION

The present invention features compositions and methods for making and using the composition for phosphorylating the 5' termini of oliogonucleotides.

One embodiment of the present invention includes a composition. The composition is represented by the formula below:

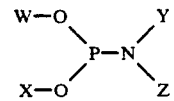

wherein if Y and Z are taken separately, each represent an alkyl, aryl, arylalkyl, cycloalkyl or cycloalkylaryl; or if Y and Z are taken together, Y and Z form an alkyl or alkylene chain with both terminal valence bonds of said chain being attached to the nitrogen atom to which Y and Z are attached; or if Y and Z are taken together, with the nitrogen atom, Y and Z form a nitrogen heterocycle including at least one additional heteroatom selected from the group consisting of nitrogen, oxygen, and sulfur. W and X are selected from the group of functional groups subject to nucleophilic attack or β-elimination.

Referring now to the situation where the nitrogen and Y and Z taken together form a saturated or unsaturated nitrogen heterocycle, the heterocycle includes tetrazole, indole, imidazole, benzimidazole and similar nitrogen heterocycles some of which are characterized by at least two ethylenic double bonds which are normally conjugated. The heterocycle may include other hetero atoms such as nitrogen, sulfur, or oxygen.

Preferably, Y and Z taken separately represent alkyl moieties of three carbons or less. A preferred alkyl moiety includes isopropyl groups.

In selecting W and X, consideration should be given to the stability of the atomic moieties at room temperature in conditions that W and X will encounter during the synthesis of oligonucleotides in automated DNA synthesis machines. Such conditions include acid reagents, such as solutions of trichloroacetic acid in dichloromethane, oxidation reagents, such as iodine in water and tetrahydrofuran, acetylating reagents, such as solutions of acetic anhydride and dimethylaminopyridine, and phosphorylating reagents, such as solutions of activated nucleoside phosphoramidites.

Preferably, W and X are selected from the group consisting of alkyl, aryl, arylalkyl, cycloalkyl, cycloalkylaryl, cyanoalkyl or haloalkyl derivatives susceptible to nucleophilic attack or β-elimination.

By way of example without limitation, referring to W and X, a preferred alkyl derivative includes alkyl chains of between one and three carbons, and most preferably methyl derivatives. A preferred cycloalkyl or cycloalkylaryl derivative includes ribose derivatives of nucleotide bases and base analogs and derivatives thereof, such as 2',3'-dibenzoyluridyl derivatives. A further preferred cycloalkylaryl derivative includes fluorenylmethoxycarbonyl (FMOC) and derivatives thereof.

By way of example without limitation, referring to W and X, preferred aryl or alkylaryl derivatives have electron withdrawing groups. Examples include halophenyl or phenol derivatives such as chlorophenyl, bromophenyl or fluorophenyl derivatives or nitrophenethyl derivatives. Preferred cyanoalkyl and haloalkyl derivatives include 2-cyanoethyl derivatives and 2,2,2-trichloro- or 2,2,2-tribromoethyl derivatives.

A further embodiment of the present inventions includes a method of phosphorylating the 5' termini of oligonucleotides. The method includes the steps of reacting the 5' terminus of an oligonucleotide with a composition represented by the formula:

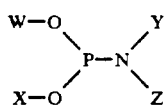

wherein W, X, Y, and Z are consistent with the previous description of the composition to form a reaction product. Next, oxidizing the reaction product to produce a phosphorylated compound.

After completion of the chain elongation and 5' terminal phosphorylation steps, the DNA is removed from the synthesis support and deblocked using conventional steps. If necessary, additional deblocking steps are added in order to completely remove the protecting groups. For example, in the case where ribonucleotide derivatives are used as blocking groups, the liberated oligonucleotide is then subjected to sequential treatment with sodium periodate and piperidine. The reaction with sodium periodate and piperidine removes the terminal ribonucleotides and the oligonucleotide is recovered bearing a terminal phosphate group.

The method of making the present compounds is further described in the following experimental examples which exemplify features of the preferred embodiments. The experimental protocol sets forth typical conditions and procedures.

EXPERIMENTAL EXAMPLES

I. Synthesis Section

A. General Methods and Materials.

All chemicals were of analytical grade and used as available from manufacturers or distributors unless otherwise indicated. Unless otherwise indicated, all chemicals are available from Aldrich Chem.

B. Synthesis of 2',3'-dibenzoyluridyl-N,N-di-isopropylaminomethoxyphosphine.

Diisopropylmethylphosphonamidic chloride (3.3g, 16.7 mmol) was added to a magnetically stirred solution of tetrahydrofuran (400 ml), diisopropylethylamine (35 ml, 200 mmol) and 2',3'-dibenzoyluridine (Sigma Chemical Co.) (11.1 mmol) at 0° C. The mixture was warmed to room temperature overnight. The hydrochloride salt formed during the reaction was removed from the reaction mixture by filtration through a scintered glass funnel. The resulting filtrate was recovered, diluted 1/1 with ethyl acetate, and washed with three 200 ml portions of 5% NaHCO$_3$. The organic portion was then dried over Na$_2$SO$_4$ and evaporated to yield the crude product as a yellow oil. The oil was dissolved in a mixture of dichloromethane/hexane/triethylamine (6/4/1 v/v/v) (50 ml) and applied to a column of silica gel (150 g) which had been equilibrated with the same solvent mixture. The column was eluted with the solvent mixture and fractions (10 ml) were collected. Fractions which contained the desired product were identified as 2',3'-dibenzoyluridyl-N,N-diisopropylaminomethoxyphosphine (hereinafter referred to as Compound I) represented by the formula set forth below:

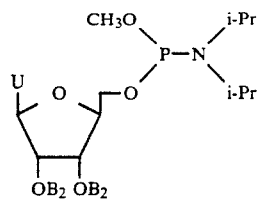

wherein U is uridyl, Bz is Benzyl and i-Pr is isopropyl (Rf=0.64 silica gel TLC developed in ethyl acetate/triethylamine 9/1). Fractions of Compound I were pooled, evaporated, and then coevaporated with toluene (3×5 ml) to yield the desired product as an oil (6.4 g, 94%).

C. Synthesis of Bis-(2-Cyanoethoxy)-N,N-Diisopropylaminomethoxyphosphine

Diisopropylamino phosphorodichloridite (made in accordance with the procedure set forth in Takeo, Shimidzu, et al. Nucleic Acid Research Symposium Series No. 12,55-58 (1983)) (14.2g, 70.0 mmol) was added to a magnetically stirred solution of tetrahydrofuran (100 ml), diisopropylethylamine (36.6 ml, 210 mmol) and 3-hydroxypropionitrile (9.6 ml, 140 mmol) at 0° C. After 4 hours, the mixture was warmed to room temperature and stirred for an additional 2 hours. The hydrochloride salt was removed from the reaction mixture by filtration through a scintered glass funnel. The resulting filtrate was recovered, diluted 1/1 with ethyl acetate, and washed with three 100 ml portions of 5% NaHCO$_3$. The organic portion was then dried over Na and evaporated to yield 17.7g of crude product as a yellow oil. The oil was dissolved in a mixture of dichloromethane/hexane/triethylamine (6/4/1 v/v/v) (50 ml) and applied to a column of silica gel (175 g) which had been equilibrated with the same solvent mixture. The column was eluted with the solvent mixture and fractions (20 ml) were collected. Fractions which contained the desired product were identified as bis-(2-cyanoethoxy)-N,N-diisopropylaminomethoxyphosphine (hereinafter referred to as Compound II) represented by formula set forth below:

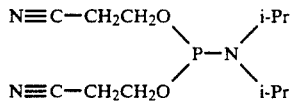

wherein i-Pr is isopropyl. (Rf=0.60 silica gel TLC developed in ethyl acetate/triethylamine 9/1). Fractions containing Component II were pooled, evaporated, and then coevaporated with toluene (3×5 ml) to yield the desired product as a colorless oil (11.1 g, 58.7%)$^{31}$p NMR=−146.75 ppm, relative to trimethylphosphate in CH$_2$Cl$_2$.

D. Synthesis of 2-Cyanoethoxymethoxy-N,N-Diisopropylaminophosphine

Diisopropylmethyl phosphoramidite chloride (10.7 g, 52.5 mmol) was added to a magnetically stirred solution of THF (100 ml), diisopropylethylamine (27.5 ml, 157.5 mmol) and 3-hydroxypropionitrile (7.2 ml, 105 mmol) at 0° C. After 4 hours, the mixture was warmed to room temperature and stirred for an additional 2 hours. The hydrochloride salt was removed from the reaction mixture by filtration through a scintered glass funnel. The resulting filtrate was recovered, diluted 1/1 with ethyl acetate, and washed with three 100 ml portions of 5% NaHCO₃. The organic portion was then dried over Na₂SO₄ and evaporated to yield the crude product which was dissolved in a mixture of dichloromethane/hexane/triethylamine (6/4/1 v/v/v) (50 ml) and applied to a column of silica gel (175 g) which had been equilibrated with the same solvent mixture. The column was eluted with the solvent mixture and fractions (20 ml) were collected. Fractions which contained the desired product were identified as 2-cyanoethoxymethoxy-N,N-diisopropylaminophosphine (hereinafter referred to as Compound III) represented by the formula set forth below:

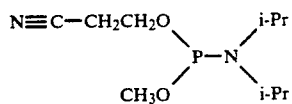

wherein i-Pr is isopropyl. Fractions containing Compound III were pooled, evaporated, and then coevaporated with toluene (3×5 ml).

E. Synthesis of Oligonucleotides having 5' Terminal Phosphate Monoesters

In a typical synthesis, the synthesizer is programmed to permit the addition of the modified phosphoramidite, such as compounds I, II and III, as they would any other phosphoramidite compound. After completion of the chain elongation steps and 5' terminal phosphorylation steps, the DNA is removed from the synthesis support and deblocked in the usual manner. To deblock the terminal phosphate triester and remove additional blocking groups, referring now to ribonucleotide blocking groups and related compounds, the liberated oligonucleotide is then subjected to a sequence of appropriate deblocking steps. For example, in the case of ribonucleotide blocking groups deblocking is accomplished with a sequential treatment with sodium periodate and piperidine as outlined below.

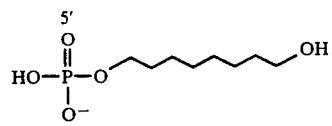

The compound 2-cyanoethoxymethoxy-N,N-diisopropylaminophosphine, does not efficiently provide the desired oligonucleotide phosphate-monoester. Complete removal of the protecting groups is difficult under normal conditions to which DNA can be subjected to.

Several fragments containing synthetic 5' phosphate group have been prepared. FIGS. 1 through 3 illustrate the HPLC characterization data which compares the synthetically phosphorylated DNA with standard samples obtained from commercial sources. Turning first to FIG. 1A describes HPLC characterization data for a commercially obtained standard sample of pT₁₂. FIG. 1B describes HPLC characterization data for a sample of pT₁₂ after synthesis with Compound II. FIG. 1C describes HPLC characterization data for a coinjection of a standard pT₁₂ sample with a pT₁₂ sample obtained using Compound II.

Turning now to FIG. 2A describes HPLC characterization data for a commercial standard sample of pT₁₂. FIG. 2B describes HPLC characterization data for a sample of synthetic UpT(pT)₁₁. FIG. 2C describes HPLC characterization data for a mixture containing synthetic UpT(pT)₁₁ and pT12 obtained after the periodate oxidation of UpT(pT)₁₁. FIG. 2D is (pT)₁₂ obtained after periodate treatment of Up(pT). FIG. 2E describes HPLC characterization data for a commercial standard sample of (pT)₁₂. Finally, FIG. 2F describes HPLC characterization data for the coinjection of a commercial standard sample of (pT)₁₂ and (pT)₁₂ obtained after oxidation of UpT(pT)₁₁.

Figure 3D:
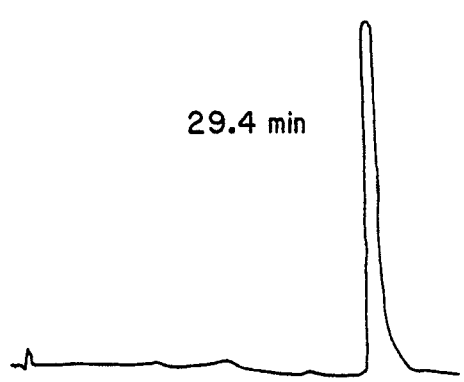
Figure 3B:
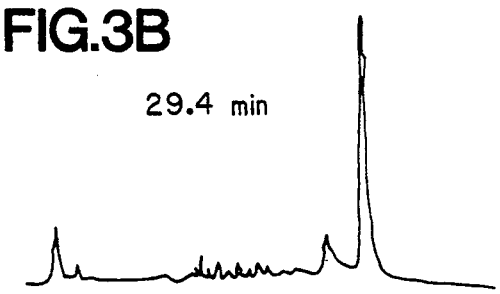
Figure 3E:
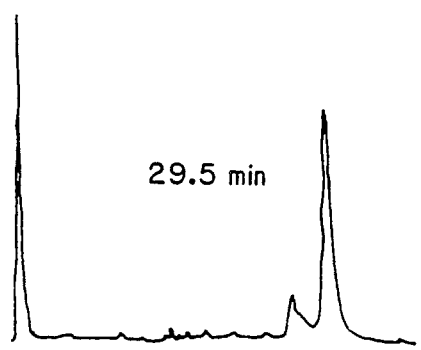

Turning now to FIG. 3A describes HPLC retention times for a commercial standard sample of (pT)₁₂. FIG. 3B describes HPLC retention time data for 5'E-DApT(pT)₁₁ obtained from ( 12 synthesized using Com-

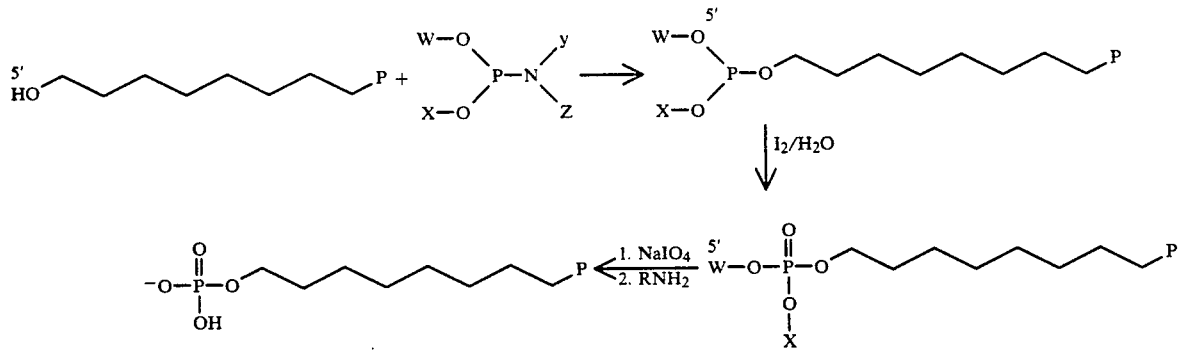

Figure 3C:
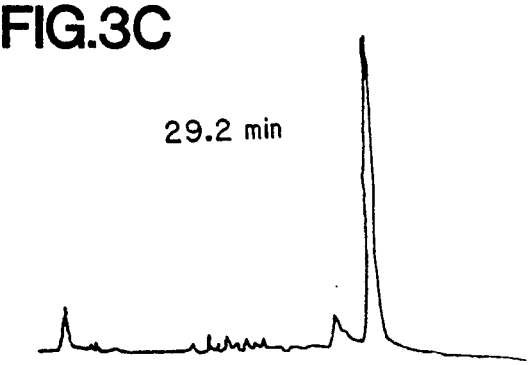

Deprotection of oligonucleotides coupled with phosphorylating agents such as compound II and related compounds can be achieved during the base debl:ocking step with ammonium hydroxide as set forth below:

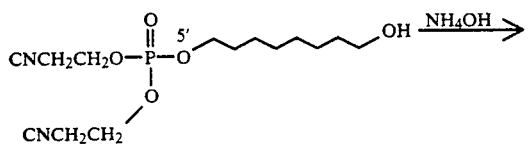

pound II. FIG. 3C describes HPLC retention time data for a coinjection of EDApT(pT)₁₁ obtained from a commercially obtained sample (pT)₁₂ and 5'-EDApT(pT)₁₁ obtained from (pT)₁₂ synthesized using Compound II. FIG. 3D describes HPLC retention time data for a commercial standard of (pT)₁₂. Finally, FIG. 3E describes HPLC retention times for 5' EDApT(pT)₁₂ obtained from ( synthesized using Compound I.

Short fragments of DNA bearing the synthetic phosphate group have been combined enzymatically to produce fragments of extended length. It should be noted, that both of the protecting groups of Compound III does not favor complete removal phosphate. Compound III is not susceptible to β-elimination of the protecting groups which appears to be a preferred method of removal.

The present methods and compounds offer improvements to synthetic DNA which can be directly synthesized bearing a 5' phosphate group. The present methods and compounds are compatible with automated DNA synthesizers and give products of high yield. The ability to directly isolate 5' phosphorylated DNA simplifies procedures required to construct artificial genes of commercial significance. The need for enzymatic phosphorylation is eliminated and the total time required to build synthetic DNA having extended length has been reduced. Synthetic fragments bearing 5' terminal phosphate groups can also be used to synthesize DNA bearing terminal amine functional groups. These fragments can then undergo subsequent modification to prepare DNA bearing nonradioactive reporter groups.

Thus, while preferred embodiments of the invention have been described, the present invention is capable of variation and modification and, therefore, the invention should not be limited to the precise details set forth, but should include such changes and alterations that fall within the purview of the following claims.

I claim:

1. A method of converting terminal 5'-hydroxyl groups of oligonucleotides into phosphate monoesters including the steps of
   a) reacting the 5' termini of an oligonucleotide with a composition represented by the formula:

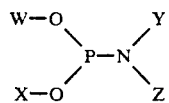

wherein Y and Z taken separately each represent an alkyl, aryl, arylalkyl, cycloalkyl, or cycloalkylaryl; or Y and Z taken together form an alkyl or alkylene chain with both terminal valence of said chain being attached to the nitrogen atom to which Y and Z are attached; or Y and Z taken together with the nitrogen atom form a saturated nitrogen heterocycle including at least one additional heteroatom selected from the group consisting of nitrogen, oxygen, and sulfur; and W and X are blocking groups selected from group of functional groups subject to nucleophilic attach or β-elimination; and,
   b) removing the blocking groups W and X.

2. The method of claim 1 wherein W and X are stable at room temperature, stable in acid reagents, oxidizing reagents, acetylating reagents and phosphorylating reagents.

3. The method of claim 1 wherein W and X are selected from the group consisting of alkyl, aryl, arylalkyl, cycloalkyl, cycloalkylaryl, cyanoalkyl or haloalkyl derivatives capable of subjection to nucleophilic attack or β-elimination.

4. The method of claim 1 wherein Y and Z taken separately represent alkyl moieties of three carbons or less.

5. The method of claim 4 wherein the alkyl moieties represent isopropyl groups.

6. The method of claim 1 wherein said blocking groups susceptible to nucleophilic attack include alkyl derivatives having three carbons or less and phenyl derivatives having electron withdrawing groups.

7. The method of claim 3 wherein said groups capable of β-elimination include haloalkyl, cyanoalkyl, alkylaryl, and cycloalkylaryl derivatives.

8. The method of claim 6 wherein said alkyl derivative is methyl.

9. The method of claim 6 wherein said phenyl derivative is selected from the group consisting of chlorophenyl, bromophenyl, and fluorophenyl derivatives.

10. A method of converting terminal 5'-hydroxyl groups of oligonucleotides into phosphate monoesters including the steps of
    a) reacting the 5' termini of an oligonucleotide with a composition represented by the formula:

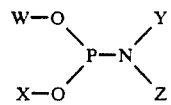

wherein Y and Z taken separately each represent an alkyl, aryl, arylalkyl, cycloalkyl, or cycloalkylaryl; or Y and Z taken together form an alkyl or alkylene chain with both terminal valence of said chain being attached to the nitrogen atom to which Y and Z are attached; or Y and Z taken together with the nitrogen atom form a saturated nitrogen heterocycle including at least one additional heteroatom selected from the group consisting of nitrogen, oxygen, an sulfur; and W is further represented by the formula:

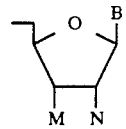

wherein B is a nucleotide base, base analog or derivative thereof and, M and N are OH or $OR_2$ in which $R_2$ is a blocking group, and X is alkyl, aryl, arylalkyl, cycloalkyl, cycloalkylaryl, cyanoalkyl or haloalkyl derivatives capable of subjection to nucleophilic attack or βelimination; and,
    b) removing the blocking groups W and X.

11. The method of claim 10 wherein Y and Z are isopropyl.

12. The method of claim 11 wherein M and N are benzyloxy.

13. The method of claim 10 wherein X is methyl.

14. A method of converting terminal 5' hydroxyl groups of oligonucleotides including the steps of
    a) reacting the 5' termini of an oligonucleotide with a composition represented by the formula:

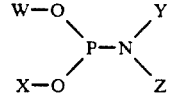

wherein Y and Z taken separately each represent an alkyl, aryl, arylalkyl, cycloalkyl, or cycloalkylaryl; or Y and Z taken together form an alkyl or alkylene chain with both terminal valence of said chain being attached to the nitrogen atom to which Y and Z are attached; or Y and Z taken together with the nitrogen atom form a saturated nitrogen heterocycle including at least one additional heteroatom selected from the group consisting of nitrogen, oxygen, and sulfur; and W and X are cyanoalkyl being a chain length of three carbons or less excluding the cyano moiety; and, b) removing the blocking groups W and X.

15. The method of claim 14 wherein W and X are cyanoethyl.

* * * * *

UNITED STATES PATENT AND TRADEMARK OFFICE
CERTIFICATE OF CORRECTION

PATENT NO. : 5,071,974
DATED : March 21, 1991
INVENTOR(S) : E. Patrick Groody

It is certified that error appears in the above-indentified patent and that said Letters Patent is hereby corrected as shown below:

Col. Line 2  44  "atomic moieties" should read functional groups;

4  34  "over Na" should read --over $Na_2SO_4$--;

6  42  "from (12 synthesized" should read --from $(pT)_{12}$ synthesized--;

6  67  "from (synthesized" should read --from $(pT)_{12}$ synthesized--;

7  4  "that both of the protecting groups of Compound III does not favor complete removal phosphate. Compound III is not susceptible to ß-elimination of the protecting groups which appears to be a preferred method of removal." should read that Compound III does not favor complete removal of the phosphate protecting groups. Both of the protecting groups of Compound III are not susceptible to ß-elimination which appears to be a preferred method of removal.--; and 8  35  "an sulfur" should read --and sulfur--.

Signed and Sealed this

Thirtieth Day of November, 1993

Attest:

BRUCE LEHMAN

Attesting Officer

Commissioner of Patents and Trademarks